United States Patent
Crea

(10) Patent No.: US 6,432,675 B1
(45) Date of Patent: *Aug. 13, 2002

(54) COMBINATORIAL POLYPEPTIDE ANTIGENS

(76) Inventor: Roberto Crea, 45 Amherst Rd., Belmont, MA (US) 02178

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/506,131

(22) Filed: Jul. 24, 1995

Related U.S. Application Data

(63) Continuation of application No. 08/292,170, filed on Aug. 16, 1994, now abandoned, which is a continuation of application No. 07/900,123, filed on Jun. 18, 1992, now abandoned.

(51) Int. Cl.$^7$ ........................ C12N 15/09; A61K 39/00; A61K 39/21; A61K 38/00
(52) U.S. Cl. ................ 435/69.3; 435/172.3; 424/184.1; 424/188.1; 424/204.1; 530/324; 530/325
(58) Field of Search ................... 424/184.1, 188.1, 424/204.1; 435/172.3, 69.3; 530/324, 325

(56) References Cited

U.S. PATENT DOCUMENTS

| | | | |
|---|---|---|---|
| 5,010,175 A | * | 4/1991 | Rutter et al. ................. 530/334 |
| 5,270,170 A | * | 12/1993 | Schatz et al. ................ 435/7.37 |

FOREIGN PATENT DOCUMENTS

| | | | |
|---|---|---|---|
| EP | 0 255 190 | 2/1988 | ............ C12N/15/00 |
| EP | 0 311 228 | 4/1989 | ............ A61K/39/21 |
| WO | WO 90/02809 | 3/1990 | ............ C12P/21/00 |
| WO | WO 90/03984 | 4/1990 | ............ C07K/7/10 |
| WO | WO 90/15078 | 12/1990 | ............ C07K/15/28 |
| WO | WO 91/86575 | 5/1991 | ............ C07K/15/28 |

OTHER PUBLICATIONS

Webster's Ninth New Collegiate Dictionary; Marriam–Webster, Inc.; p. 1000, 1991.*
Harlow et al.; Antibodies–a laboratory manual; pp. 96–97, 1988.*
Holley, et al, 1991, PNAS 88: 6800–6804, 1991.*
Oram, et al, AIDS Res. Hum. Retroviruses, 1991.*
Wolinsky, et al, Science 255: 1134–1136, 1992.*
LaRosa, Science 249: 932–935, 1990.*
Holley, et al, 1991, PNAS 88: 6800–6804.*
Oram, et al, 1991, AIDS Res. Hum. Retro. 7(7):605–614.*
Wolinsky, et al, 1992, Science 255: 1134–1136.*
LaRosa, 1990, Science 249: 932–935.*
Hwang, et al, 1991, Science 253: 71–74.*
Hwang, et al, 1991, Identification of the envelope V3 loop as the . . . Science 253: 71–74.*
Rusche, J., "Antibodies that Inhibit Fusion of Human Immunodeficiency Virus–infected Cells Bind a 24–Amino acid sequence of the Viral Envelope, gp120", *PNAS*, vol. 85, pp. 3198–3202 (1988).
(1992) *J. Virol. 66*:2570 K. Schlienger.
(1992) *Bio/technol. 10*:297 Adam P. Arkin.
(1992) *Science 255*:1134 Steven M. Wolinsky.
(1992) *J. Immunol. 148*:914 Bernardetta Nardelli.
(1992) *Science 255*:333 Hidemi Takahashi.
(1992) *Virology 187*:423 Lucinda A. Ivanoff.
(1992) *T.I.B.S. 17*:191 S. Putney.
(1991) *PNAS 88*:10726 Tsuneya Ohno.
(1991) *AIDS Res. Human Retroviruses 7*:605 J.D. Oram.
(1991) *PNAS 88*:6800 L. Howard Holley.
(1991) *Res. Virol. 142*:247 S.A. Tilley.
(1991) *AIDS Res. Human Retroviruses 7*:595 Lucinda Ivanoff.
(1991) *Immund. 73*:371 P.A. Broliden.
(1990) *J. Virol. 64*:5797 Gillian M. Air.
(1990) *Science 250*:1590 Kashi Javaherian.
(1990) *Nature 347*:18 Simon Wain–Hobson.
(1990) *Science 249*:932 Gregory J. LaRosa.
(1988) *PNAS 85*:3198 James R. Rusche.
(1988) *PNAS 85*:1932 Thomas J. Palker.
(1988) *Nature 333*:573 T.F. Smith.
(1985) *Nature 316*:212 F.E.G. Cox.
(1983) *PNAS 80*:4527 Mark Krystal.
(1983) *J. Virol. 48*:52 Gerald W. Both.
Reidhaar–Olson and Sauer "Combinatorial Cassette Mutagenesis as a Probe of the Informational Content of Protein Sequences" Science 1988, vol. 241, pp. 53–57.
International Search Report.

* cited by examiner

Primary Examiner—Hankyel T. Park
(74) Attorney, Agent, or Firm—Lahive & Cockfield, LLP; Giulio A. DeConti, Jr. Esq.; Jeanne M. DiGiorgio, Esq

(57) ABSTRACT

The invention provides a method of generating a set of polypeptide antigens derived from a protein (or portion thereof) which is expressed with some degree of sequence heterogeneity among naturally or artificially induced variants of the protein. The purpose is to provide a mix of antigens which can be used to immunize against the variants and, preferably, possible unknown or new variants that may arise.

13 Claims, No Drawings

COMBINATORIAL POLYPEPTIDE ANTIGENS

This application is a continuation application of Ser. No. 08/292,170, filed Aug. 16, 1994 (abandoned), which in turn is a continuation of Ser. No. 07/900,123, filed Jun. 18, 1992, (abandoned). The contents of all of the aforementioned application(s) are hereby incorporated by reference.

BACKGROUND OF THE INVENTION

Host defense is a hallmark of vertebrate immune systems. To this end, antibodies perform numerous functions in the defense against pathogens. For instance, antibodies can neutralize a biologically active molecule, induce the complement pathway, stimulate phagocytosis (opsonization), or participate in antibody-dependent cell-mediated cytotoxicity (ADCC).

If the antibody binds to a site critical for the biological function of a molecule, the activity of the molecule can be neutralized. In this way, specific antibodies can block the binding of a virus or a protozoan to the surface of a cell. Similarly, bacterial and other types of toxins can be bound and neutralized by appropriate antibodies. Moreover, regardless of whether a bound antibody neutralizes its target, the resulting antigen-antibody complex can interact with other defense mechanisms, resulting in destruction and/or clearance of the antigen.

Parasites have evolved an array of mechanisms for avoiding an immune response. Antigenic variation is perhaps the most studied of the evasion strategies, in part because such variation makes vaccine development especially difficult. Generally, here are two ways in which antigenic variation can occur: antigenic drift and antigenic shift. Antigenic drift is relatively straightforward. Point mutations arise in genes that encode pathogen antigens, altering some of the epitopes on the antigen such that host immunologic memory to the original antigen is not triggered by the mutant. As immunity to one variant will not necessarily ensure immunity to others, accumulation of such point mutations in a pathogen population can result in multiple infections in the same host. Antigenic drift has been found in most pathogens (including viruses, bacteria, and protozoa), its importance varying among individual species.

Many viruses are capable of great antigenic variation, and large numbers of serologically distinct strains of these viruses have been identified. As a result, a particular strain of a virus becomes insusceptible to immunity generated in the population by previous infection or vaccination. For instance, the progress of HIV-1 vaccine development has been impeded by the amino acid sequence variability among different isolates of HIV-1. This variability is particularly high in the external envelope protein gp120, which is the primary target for antibodies that neutralize virus infectivity (Robey et al. (1986) *PNAS* 83:7023; Putney et al. (1986) *Science* 234:1392; and Rusche et al. (1987) *PNAS* 84:6924, incorporated by reference herein). Studies in humans and mice have revealed a small region of gp120, termed the V3 loop or principal neutralizing determinant (PND), comprising bout 35 residues between two invariant, disulfide-crosslinked cysteines (Cys-303 to Cys-338: HIV-1 nomenclature of Takahashi et al. (1992) *Science* 255:333), that evokes the major neutralizing antibodies to the virus (Palker et al. (1988) *PNAS* 85:1932; Rusche et al. (1988) *PNAS* 85:3198 and Goudsmit et al. (1988) *PNAS* 85:4478). While this same region is one of the most variable in sequence among different clonal isolates (Takahashi et al. (1992) *Science* 255:333), analysis of the amino acid sequences of this domain revealed conservation to better than 80-percent of the amino acids in 9 out of 14 positions in the central portion of the V3 loop, suggesting that there are constraints on the V3 loop variability (LaRosa et al. (1990) *Science* 249:932). However, because of this variability, neutralizing antibodies elicited by the PND from one isolate generally do not neutralize isolates with PND's of different amino acid sequence.

Likewise, attempts to control influenza by vaccination has so far been of limited success and are hindered by continual changes in the major surface antigen of influenza viruses, the hemagglutinin (HA) and neuraminidase (NA), against which neutralizing antibodies are primarily directed (Caton et al.(1982) *Cell* 31:417; Cox et al. (1983) *Bulletin W.H.O.* 61:143; Eckert, E. A. (1972) *J. Virology* 11:183). The influenza viruses have the ability to undergo a high degree of antigenic variation within a short period of time. It is this property of the virus that has made it difficult to control the seasonal outbreaks of influenza throughout the human and animal populations.

Through seralogic and sequencing studies, two types of antigenic variations have been demonstrated in influenza A viruses. Antigenic shift occurs primarily when either HA or NA, or both, are replaced in a new viral strain with a new antigenically novel HA or NA. The occurrence of new subtypes created by antigenic shift usually results in pandemics of infection.

Antigenic drift occurs in influenza viruses of a given subtype. Amino acid and nucleotide sequence analysis suggests that antigenic drift occurs through a series of sequential mutations, resulting in amino acid changes in the polypeptide and differences in the antigenicity of the virus. The accumulation of several mutations via antigenic drift eventually results in a subtype able to evade the immune response of a wide number of subjects previously exposed to a similar subtype. In fact, similar new variants have been selected experimentally by passage of viruses in the presence of small amounts of antibodies in mice or chick embryos. Antigenic drift gives rise to less serious outbreak, or epidemics, of infection. Antigenic drift has also been observed in influenza B viruses.

Purified antigen vaccines directed against the hepatitis B virus currently in clinical trials generally consists of antigens of a single viral subtype. The rational for this decision has been that both S region and pre-S(2) region-specific antibodies, shown to be somewhat effective in neutralizing the hepatitis B virus, are primarily group-specific. However, this logic does not take into consideration the influence of viral subtype on T-cell recognition. It has been demonstrated that murine pre-S(2)-specific T-cell response is highly subtype-specific (Milic H. et al. (1990) *J. Immunol.* 144:3535).

The unicellular protozoon *Plasmodium falciparum* is the predominant pathogen causing malaria in humans. The infection starts when sporozoites, present in the salivary glands of Anopheles mosquitos, are inoculated into the blood of susceptible hosts. Sporozoites rapidly penetrate hepatocytes, in which they further develop into liver schizonts. After maturation, infectious merozoites are released into the blood of the host and invade erythrocytes, starting a new schizogonic cycle that is associated with the clinical symptoms of malaria. The number of malaria cases predicted by the World Health Organization is over 100 million worldwide.

Limited success has been reported in the protection of monkeys against infection by certain species of Plasmodium by immunization with purified surface antigens expressed during at least one stage of the life cycle of the parasite. For instance, an attractive candidate for a blood-stage vaccine is the merozoite protein termed p190, or polymorphic schizont antigen (Herra et al. (1992) *Infection and Immunity* 60:154–158; Merkli et al. (1984) *Nature* 311:379–382; Mackay et al. (1985) *EMBO J*. 4:3823–3829). p190 is a large glycoprotein which is synthesized and extensively processed during merozoite formation, the 80 kDa processing product of which is the major coat protein of mature merozoites. Monoclonal antibody probes against P190 and primary sequence analysis reveal that the antigen contains polymorphic sequences giving rise to antigenic variation among species and subspecies of Plasmodium.

SUMMARY OF THE INVENTION

This invention pertains to a set of polypeptide antigens having amino acid sequences derived from amino acid sequences of a population of variants of a protein, or a portion thereof, and to methods of producing the set of polypeptide antigens. In general, the method comprises:

a. selecting a protein, or a portion thereof, which exhibits a population of N variants, represented by the formula $$A_1A_2A_3 \ldots A_{n-2}A_{n-1}A_n,$$

where $A_n$ is an amino acid occurring at amino acid position n of the protein, or portion thereof;

b. determining the number of times $O^{aa}_n$ each type of amino acid occurs at each amino acid position n in the N variants;

c. calculating the frequency of occurrence $(O^{aa}_n/N)_n$ of each type of amino acid at each amino acid position n in the N variants; and d. generating a set of polypeptide antigens having amino acid sequences represented substantially by the formula; and $$A'_1A'_2A'_3 \ldots A'_{n-2}A'_{n-1}A'_n$$

where $A'_n$ is defined as an amino acid type which occurs at greater than a selected frequency at the corresponding amino acid position in the N variants.

In a preferred embodiment, the set of polypeptide antigens is generated by determining a degenerate oligonucleotide sequence having a minimum number of nucleotide combinations at each codon position n which combinations include at least the codons coding for each type of amino acid $A'_1$ to $A'_n$. The degenerate oligonucleotide is incorporated into an expressible gene to create a gene set. The gene set is expressed in an appropriate expression system to generate the set of polypeptide antigens:

$$A'_1A'_2A'_3 \ldots A'_{n-2}A'_{n-1}A'_n$$

Typically, n will range from 8 to about 150. The threshold frequency selected for inclusion of an amino acid in the set of polypeptide antigens at a given position can be set at the same value for all amino acid positions. Alternatively, the selected frequency threshold can be set individually for each amino acid position and can vary from position to position. Typically the threshold frequency will range from 5–15%. This means that for inclusion of a particular amino acid at a given position in the set of polypeptide antigens generated, the amino acid must appear in that position in more than 5–15% of the N variants (i.e., $O^{aa}_n/N$ must be greater than 5–15%).

The set of polypeptide antigens can correspond to an entire peptide sequence of a protein, or to only a portion thereof. In addition, the variant sequence need not be contiguous in the protein; it can be dispersed within a single protein or protein subunit or in more than one protein or protein subunit.

The set of polypeptides can be used as an artificial vaccine. The antigens can be administered to the host organism in a physiologically acceptable vehicle and under a dosage regimen sufficient to create protective immunity against a population of variants of the antigen. For instance, if the protein is a component of a pathogen, the protein or portion thereof may include sequences comprising one or more neutralizing epitopes such that the set of polypeptide antigens, when administered as an immunogen, results in the production of neutralizing antibodies to the pathogen by a host organism.

Alternatively, the form as well as the route of administration of the set of polypeptide antigens can be adjusted so as to be tolerogenic and thereby create artificial tolerance in a host organism to a variant protein antigen, or a portion thereof.

DETAILED DESCRIPTION OF THE INVENTION

Either clinically evident or inapparent infection by a pathogen can lead to immunity, and the immunity to pathogens of the same antigenic structure appears to be long-lasting. However, reinfection by the pathogen can be caused by variants with minor antigenic differences. Further, as immunity is highly epitope-specific, artifically-induced immunity to a pathogen is often limited by marked antigenic variation of the pathogen. Therefore, the ability of a pathogen to undergo antigenic drift often results in the ineffectiveness of a conventional vaccine.

This invention provides a method of generating a set of polypeptide antigens derived from a protein (or portion thereof) which is expressed with some degree of sequence heterogeneity among naturally or artificially induced variants of the protein. The purpose is to provide a mix of antigens which can be used to immunize against the variants and, preferably, possible unknown or new variants that may arise.

According to the method of this invention, the frequency of occurrence for each amino acid type is determined for each amino acid position of the protein (or a portion of the protein) in the population of variants. Amino acids which appear at each position above a predetermined frequency in the population of variants (e.g., 5%, 10%, 15%, etc.) are selected for inclusion to generate the set of polypeptide antigens.

In general, polypeptides will range from 8 to 150 amino acids, preferably from about 10 to 50 amino acids, in length.

In the preferred embodiment, the set of polypeptide antigens is produced by way of a degenerate oligonucleotide. The sequence of the degenerate oligonucleotide can be determined so as to yield the minimum number of nucleotide combinations, for each codon necessary to give rise to each amino acid type selected for inclusion (i.e., those occuring at greater than a selected freguency at the corresponding amino acid position n in the population of variants).

The mixture of synthetic oligonucleotides can be enzymatically ligated into gene sequences such that the set of polypeptide antigens are expressible as individual polypeptides, or as a set of larger fusion proteins containing the set of polypeptide antigens therein. Alternatively, the set of polypeptide antigens can be generated by organochemical peptide synthesis. Each round of amino acid coupling can be carried out to yield a determined heterogeneity of amino acid types (by including more than one activated amino acid at appropriate steps in the synthesis) at a given amino acid position. The amino acid mix is based on the frequency analysis of the N variants. Alternatively, the amino acid mix can be determined based upon the nucleotide (codon) combination generated in making the degenerate oligonucleotide.

The combinatorial effect arising from the use of degenerate oligonucleotide sequences will typically give rise to some amino acid types which do not occur in the original population of variants. This provides for the generation of polypeptides, within the overall set of polypeptide antigens, which may not have arisen in nature. Because these nucleotide combinations are based initially on known variants, the codons which arise for additional amino acids potentially represent mutations more probable in nature, rather than those artificially created by a structural analysis of the protein. Thus, the set of polypeptide antigens can result in immunity to a wide range of potential variants as well as to known variants of the protein.

To analyze the sequences of a population of variants of a protein, the amino acid sequences of interest can be aligned relative to sequence homology. The presence or absence of amino acids from an aligned sequence of a particular variant is relative to a chosen consensus length of a reference sequence, which can be real or artificial. In order to maintain the highest homology in alignment of sequences, deletions in the sequence of a variant relative to the reference sequence can be represented by an amino acid space (*), while insertional mutations in the variant relative to the reference sequence can be disregarded and left out of the sequence of the variant when aligned. For instance, demonstrated below are two possible alignments of three sequences of the V3 loop of HIV isolates of known tropism (Hwang et al. (1991) *Science* 253:71–76).

The sequences,

```
BaL (SEQ ID NO:1)         -CTRPNNNTRKSIHIGPGRALYTTGEIIGDIRQAHC-

HTLV-IIIB (SEQ ID NO:2)   -CTRPNNNTRKKIRIQRGPGRAFVTIGKIGNMRQAHC-

SF162 (SEQ ID NO:3)       -CTRPNNNTRKSITIGPGRAFYATGDIIGDIRQAHC-
``` can be aligned as:

```
                              1         10        20        30
                              |         |         |         |
BaL       (SEQ ID NO:1)    -CTRPNNNTRKSIHI**GPGRALYTTGEIIGDIRQAHC-
HTLV-IIIB (SEQ ID NO: 2)   -CTRPNNNTRKKIRIQRGPGRAFVTIGK*IGNMRQAHC-
SF162     (SEQ ID NO: 3)   -CTRPNNNTRKSITI**GPGRAFYATGDIIGDIRQAHC-
``` in which residue 15 and 16 of the original HTLV-IIIB strain are included in the alignment, or alternatively as:

```
                              1         10        20        30
                              |         |         |         |
BaL       (SEQ ID NO:1)    -CTRPNNNTRKSIHIGPGRALYTTGEIIGDIRQAHC-
HTLV-IIIB (SEQ D NO: 2)    -CTRPNNNTRKKIRIGPGAFVTIGK*IGNMRQAHC-
SF168     (SEQ ID NO: 3)   -CTRPNNNTRKSITIGPGRAFYATGDIIGDIRQAHC-
``` in which residues 15 and 16 of the original HTLV-IIIB strain are discarded from the alignment of the sequences.

Given N variants of the protein, the number of times $O^{aa}_n$ which a given amino acid (aa) occurs at a given position n, the frequency of occurrence for that amino acid at that position n is calculated by $O^{aa}_n/N$. The frequency at which an amino acid deletion occurs at a given position can be factored into this calculation as well.

Alternatively, if the deletions are not considered in the frequency calculation, then it may be desirable that the value of N used in the calculation at a given amino acid position n should be the number of variants less the number of variants in which an amino acid space is present at that given position. Thus, in the first example of alignment, $O^Q_{16}/N=0.333$ (33%) and $O^*_{16}/N=0.667$ (67%) if the amino acid space is defined as an amino acid type, and $O^Q_{16}/N=1.0$ (100%) if it is not.

Based upon the determination of the frequency of occurrence of amino acid types at each position n in the population of variants, a "threshold value" for inclusion of a particular amino acid type at the corresponding position n for the set of polypeptide antigens is determined. A degenerate oligonucleotide sequence can then be created. The degenerate oligonucleotide sequence is designed to have the minimum number of nucleotide combinations necessary, at each codon position, to give rise to codons for each amino acid type selected based upon the chosen threshold value.

Thus, if the population of N variants is represented by the general formula, $$A_1A_2A_3 \ldots A_{n-2}A_{n-1}A_n,$$

where each variable $A_n$ represents an amino acid occurring at the $n^{th}$ amino acid position of the protein, then a set of polypeptide antigens generated from the degenerate oligonucleotide sequence can be represented by the general formula, $$A'_1A'_2A'_3 \ldots A'_{n-2}A'_{n-1}A'_n$$

where each variable $A'_n$ represents an amino acid type coded for by a possible nucleotide combination at the corresponding codon position n in the degenerate oligonucleotide sequence.

The threshold frequency used to select types of amino acids for inclusion in the set of polypeptide antigens and accordingly, for determining the degenerate oligonucleotide sequence, can be applied uniformly to each amino acid position. For instance, a threshold value of 15 percent can be applied across the entire protein sequence. Alternatively, the threshold value can be set for each amino acid position n independently. For example, the threshold value can be set at each amino acid position n so as to include the most commonly occurring amino acid types, e.g., those which appear at that position in at least 90% of the N variants.

It may in some instances be desirable to apply a further criterion to the determination of a degenerate oligonucleotide sequence which comprises restricting the degeneracy of a codon position such that no more than a given number of amino acid types can arise at the corresponding amino acid position in the set of polypeptide antigens. For example, the degenerate sequence of a given codon position n can be restricted such that selected amino acids will occur in at least about 11% of the polypeptides of the polypeptide antigen set. This means that all of the possible nucleotide combinations of that degenerate codon will give rise to no more than 9 different amino acids at the position. Thus, the frequency at which a particular amino acid appears at a given position will depend on the possible degeneracy of the corresponding codon position. Preferably, the number will be 11.1 (9 different amino acids), 12.5 (8 different amino acids), 16.6 (6 different amino acids), 25 (4 different amino acids) or 50 (2 different amino acids).

Likewise, criteria used for choosing the population of variants for frequency analysis can be determined by such factors as the expected utility of the polypeptide antigen set and factors concerning vaccination or tolerization. For example, analysis of a variant protein sequence can be restricted to subpopulations of a larger population of variants of the protein based on factors such as epidemiological data, including geographic occurrence or alternatively, on known allele families (such as variants of the DQ HLA class II allele). Likewise, in the case of protein components of pathogens, the population of variants selected for analysis can be chosen based on known tropisms for a particular susceptible host organism.

There are many ways by which the set of polypeptide antigens can be generated from the degenerate oligonucleotide sequence. Chemical synthesis of a degenerate oligonucleotide can be carried out in an automatic DNA synthesizer, and the synthetic oligonucleotides can then be ligated into an appropriate gene for expression. A start codon (ATG) can be engineered into the sequence if desired. The degenerate oligonucleotide sequences can be incorporated into a gene construct so as to allow expression of a protein consisting essentially of the set of polypeptide antigens. Alternatively, the set of polypeptide antigens can be expressed as parts of fusion proteins. The gene library created can be brought under appropriate transcriptional control by manipulation of transcriptional regulatory sequences. It may be desirable to create fusion proteins containing a leader sequence which directs transport of the recombinant proteins along appropriate cellular secretory routes.

Various methods of chemically synthesizing polydeoxynucleotides are known, including solid-phase synthesis which, like peptide synthesis, has been fully automated in commercially available DNA synthesizers (See the Itakura et al. U.S. Pat. No. 4,598,049; the Caruthers et al. U.S. Pat. No. 4,458,066; and the Itakura U.S. Pat. Nos. 4,401,796 and 4,373,071, incorporated by reference herein).

The purpose of a degenerate set of oligonucleotides is to provide, in one mixture, all of the sequences encoding the desired set of polypeptide antigens. It will generally not be practical to synthesize each oligonucleotide of this mixture one by one, particularly in the case of great numbers of possible variants. In these instances, the mixture can be synthesized by a strategy in which a mixture of coupling units (nucleotide monomers) are added at the appropriate positions in the sequence such that the final oligonucleotide mixture includes the sequences coding for the desired set of polypeptide antigens. Conventional techniques of DNA synthesis take advantage of protecting groups on the reactive deoxynucleotides such that, upon incorporation into a growing oligomer, further coupling to that oligomer is inhibited until a subsequent deprotecting step is provided. Thus, to create a degenerate sequence, more than one type of deoxynucleotide can be simultaneously reacted with the growing oligonucleotide during a round of coupling, either by pre-mixing nucleotides or by programming the synthesizer to deliver appropriate volumes of nucleotide-containing reactant solutions. For each codon position corresponding to an amino acid position having only one amino acid type in the eventual set of polypeptide antigens, each oligonucleotide of the degenerate set of oligonucleotides will have an identical nucleotide sequence. At a codon position corresponding to an amino acid position at which more than one amino acid type will occur in the eventual set, the degenerate set of oligonucleotides will comprise nucleotide sequences giving rise to codons which code for those amino acid types at that position in the set. In some instances, due to other combinations that the degenerate nucleotide sequence can have, the resulting oligonucleotides will have codons directed to amino acid types other than those designed to be present based on analysis of the frequency of occurrence in the variant. The synthesis of degenerate oligonucleotides is well known in the art (see for example Narang, S A (1983) *Tetrahedron* 39:3; Itakura et al. (1981) in *Recombinant DNA, Proc 3rd Cleveland Sympos. Macromolecules,* ed. A G Walton, Amsterdam: Elsevier pp273–289; Itakura at al. (1984) *Annu. Rev. Biochem,* 53:323; Itakura et al (1984) *Science* 198:1056; Ike et al. (1983) *Nucleic Acid Res.* 11:477, incorporated by reference herein).

To further illustrate this technique, as is well known in the art, genes that code for proteins specify amino acid sequence by the order of deoxyribonucleotides in the DNA, but more directly by the sequence of ribonucleotides in their mRNA transcripts. An important feature of the genetic code is that all but two amino acids are encoded by more than one nucleotide triplet (codon). The genetic code (in terms of deoxyribonucleotides) can be depicted as follows:

TABLE 1

| First Position (5') | | Second Position | | Third Position (3') |
|---|---|---|---|---|
| | T | C | A | G |
| T | Phe Ser Tyr Cys | | | T |
| | Phe Ser Tyr Cys | | | C |
| | Leu Ser Stp Stp | | | A |
| | Leu Ser Stp Trp | | | G |
| C | Leu Pro His Arg | | | T |
| | Leu Pro His Arg | | | C |
| | Leu Pro Gln Arg | | | A |
| | Leu Pro Gln Arg | | | G |
| A | Ile Thr Asn Ser | | | T |
| | Ile Thr Asn Ser | | | C |
| | Ile Thr Lys Arg | | | A |
| | Met Thr Lys Arg | | | G |
| G | Val Ala Asp Gly | | | T |
| | Val Ala Asp Gly | | | C |
| | Val Ala Glu Gly | | | A |
| | Val Ala Glu Gly | | | G |

*Stp= stop codon

As noted above, one strategy of synthesizing the degenerate oligonucleotide involves simultaneously reacting more than one type of deoxynucleotide during a given round of coupling. For instance, if either a Histidine (His) or Threonine (Thr) was to appear at a given amino acid position, the synthesis of the set of oligonucleotides could be carried out as follows: (assuming synthesis were proceeding 3' to 5') the growing oligonucleotide would first be coupled to a 5'-protected thymidine deoxynucleotide, deprotected, then simultaneously reacted with a mixture of a 5'-protected adenine deoxynucleotide and a 5'-protected cytidine deoxynucleotide. Upon deprotection of the resulting oligonucleotides, another mixture of a 5'-protected adenine deoxynucleotide and a 5'-protected cytidine deoxynucleotide are simultaneously reacted. The resulting set of oligonucleotides will contain at that codon position either ACT (Thr), AAT (Asn), CAT (His) or CCT (Pro). Thus, when more than one nucleotide of a codon is varied, the use of nucleotide monomers in the synthesis can potentially result in a mixture of codons including, but not limited to, those designed to be present by frequency analysis.

Table 1 can be employed to calculate degenerate nucleotide sequences having possible combinations corresponding to codons for given amino acid types such that, at degenerate codon positions, the number of amino acid types beyond those selected by frequency analysis is minimized. For use in designating degenerate oligonucleotide sequences, and pursuant to 37 CFR §1.822(b)(1), the following symbols and meanings are provided:

TABLE 2

| Symbol | Corresponds to |
|---|---|
| A | A: adenine |
| C | C: cytosine |
| G | G: quanine |
| T | T: thymine |
| M | A or C |
| R | A or G |
| W | A or T |
| S | C or G |
| Y | C or T |
| K | G or T |
| V | A or C or G; not T |
| H | A or G or T; not G |
| D | A or G or T; not C |
| B | C or G or T; not A |
| N | A or C or G or T or unknown |

To create an amino acid space (deletion) at a given amino acid position, a portion of the oligonucleotide mixture can be held aside during the appropriate rounds of nucleotide additions (i.e., three coupling rounds per codon) so as to lack a particular codon position all together, then added back to the mixture at the start of synthesis of the subsequent codon position.

The entire coding sequence for the polypeptide antigen set can be synthesized by this method. In some instances, it may be desirable to synthesize degenerate oligonucleotide fragments by this method, which are then ligated to invariant DNA sequences synthesized separately to create a longer degenerate oligonucleotide.

Likewise, the amino acid positions containing more than one amino acid type in the generated set of polypeptide antigens need not be contiguous in the polypeptide sequence. In some instances, it may be desirable to synthesize a number of degenerate oligonucleotide fragments, each fragment corresponding to a distinct fragment of the coding sequence for the set of polypeptide antigens. Each degenerate oligonucleotide fragment can then be enzymatically ligated to the appropriate invariant DNA sequences coding for stretches of amino acids for which only one amino acid type occurs at each position in the set of polypeptide antigens. Thus, the final degenerate coding sequence is created by fusion of both degenerate and invariant sequences.

These methods are useful when the frequency-based mutations are concentrated in portions of the polypeptide antigen to be generated and it is desirable to synthesis long invariant nucleotide sequences separately from the synthesis of degenerate nucleotide sequences.

Furthermore, the degenerate oligonucleotide can be synthesized as degenerate fragments and ligated together (i.e., complementary overhangs can be created, or blunt-end ligation can be used). It is common to synthesize overlapping fragments as complementary strands, then annealing and filling in the remaining single-stranded regions of each strand. It will generally be desirable in instances requiring annealing of complementary strands that the junction be in an area of little degeneracy.

The nucleotide sequences derived from the synthesis of a degenerate oligonucleotide sequence and encoding the set of polypeptide antigens can be used to produce the set of polypeptide antigens via microbial processes. Ligating the sequences into a gene construct, such as an expression vector, and transforming or transfecting into hosts, either eukaryotic (yeast, avian or mammalian) or prokaryotic (bacterial cells), are standard procedures used in producing other well-known proteins, e.g. insulin, interferons, human growth hormone, IL-1, IL-2, and the like. Similar procedures, or obvious modifications thereof, can be employed to prepare the set of polypeptide antigens by microbial means or tissue-culture technology in accord with the subject invention.

As stated above, the degenerate set of oligonucleotides coding for the set of polypeptide antigens in the form of a library of gene constructs can be ligated into a vector suitable for expression in either prokaryotic cells, eukaryotic cells, or both. Expression vehicles for production of the set of polypeptide antigens of this invention include plasmids or other vectors. For instance, suitable vectors for the expression of the degenerate set of oligonucleotides include plasmids of the types: pBR322, pEMBL plasmids, pEX plasmids, pBTac plasmids and pUC plasmids for expression in prokaryotic cells, such as E. coli.

A number of vectors exist for the expression of recombinant proteins in yeast. For instance, YEP24, YIP5, YEP51, YEP52 and YRP17 are cloning and expression vehicles useful in the introduction of genetic constructs into S. cerevisiae (see for example Broach et al. (1983) in *Experimental Manipulation of Gene Expression,* ed M. Inouye Academic Press, p. 83, incorporated by reference herein). These vectors can replicate in E. coli due the presence of the pBR322 ori, and in S. cerevisiae due to the replication determinant of the yeast 2 micron plasmid. In addition, drug resistance markers such as ampicillin can be used.

The preferred mammalian expression vectors contain both prokaryotic sequences to facilitate the propagation of the vector in bacteria, and one or more eukaryotic transcription units that are expressed in eukaryotic cells. The pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. These vectors are modified with sequences from bacterial plasmids such as pBR322 to facilitate replication and drug resistance selection in both prokaryotic and eukaryotic cells. Alternatively, derivatives of viruses such as the bovine papilloma virus (BPV-1), Epstein-Barr virus (pHEBo and p205) can be used for transient expression of proteins in eukaryotic cells. The various methods employed in the preparation of the plasmids and transformation of host organisms are well known in the art. For other suitable expression systems for both prokaryotic and eukaryotic, as well as general recombinant procedures, see *Molecular Cloning,* 2nd Ed., ed. by Sambrook, Fritsch and Maniatis (Cold Spring Harbor Laboratory Press:1989) incorporated by reference herein.

To express the library of gene constructs of the degenerate set of oligonucleotides, it may be desirable to include transcriptional and translational regulatory elements and other non-coding sequences to the expression construct. For instance, regulatory elements including constituitive and inducible promoters and enhancers can be incorporated.

In some instances, it will be necessary to add a start codon (ATG) to the degenerate oligonucleotide sequence. It is well known in the art that a methionine at the N-terminal position can be enzymatically cleaved by the use of the enzyme methionine aminopeptidase (MAP). MAP has been cloned from E. coli (Ben-Bassat et al. (1987) *J. Bacteriol.* 169:751–757) and *Salmonella typhimurium* and its in vitro activity has been demonstrated on recombinant proteins (Miller et al. (1987) *PNAS* 84:2718–1722). Therefore, removal of an N-terminal methionine if desired can be achieved either in vivo by expressing the set of polypeptide antigens in a host which produces MAP (e.g., E. coli or CM89 or S. cerevisiae) or in vitro by use of Purified MAP (e.g., procedure of Miller et al.).

Alternatively, the coding sequences for the polypeptide antigens can be incorporated as a part of a fusion gene including an endogenous protein for expression by the microorganism. For example, the VP6 capsid protein of rotavirus can be used as an immunologic carrier protein for the polypeptide antigen set, either in the monomeric form or in the form of a viral particle. The set of degenerate oligonucleotide sequences can be incorporated into a fusion gene construct which includes coding sequences for a late vaccinia virus structural protein to produce a set of recombinant viruses expressing fusion proteins comprising the set of polypeptide antigens as part of the virion. It has been demonstrated with the use of V-3 loop/Hepatitis B surface antigen fusion proteins that recombinant Hepatitis B virions can be utilized in this role as well. Similarly, chimeric constructs coding for fusion proteins containing the set of polypeptide antigens and the poliovirus capsid protein can be created to enhance immunogenecity of the set of polypeptide antigens. The use of such fusion protein expression systems to establish a set of polypeptide antigens has the advantage that often both B-cell proliferation in response to the immunogen can be elicited. (see for example EP Publication No. 0259149; and Evans et al. (1989) *Nature* 339:385; Huang at al. (1988) *J. Virol.* 62:3855; and Schlienger et al. (1992) *J. Virol.* 66:2, incorporated by reference herein). The Multiple Antigen Peptide (MAP) system for peptide-based vaccines can be utilized in which the polypeptide antigen set is obtained directly from organochemical synthesis of the peptides onto an oligomeric branching lysine core (see for example Posnett et al. (1988) *JBC* 263:1719 and Nardelli et al. (1992) *J. Immunol.* 148:914, incorporated by reference herein). Foreign antigenic determinants can also be expressed and presented by bacterial cells.

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. Alternatively, the fusion gene can be synthesized by conventional techniques including automated DNA synthesizers.

An alternative approach to generating the set of polypeptide antigens is to carry out the peptide synthesis directly. At each codon position n in the degenerate oligonucleotide, each possible nucleotide combination can be determined and the corresponding amino acid designated for inclusion at the corresponding amino acid position of the polypeptide antigen set. Thus, synthesis of a degenerate polypeptide sequence can be directed in which sequence divergence occurs at those amino acid positions at which more than one amino acid is coded for in the corresponding codon position of the degenerate oligonucleotide. Organo-chemical synthesis of polypeptides is well known and can be carried out by procedures such as solid state peptide synthesis using automated protein synthesizers.

The synthesis of polypeptides is generally carried out through the Condensation of the carboxy group of an amino acid, and the amino group of another amino acid, to form a peptide bond. A sequence can be constructed by repeating the condensation of individual amino acid residues in stepwise elongation, in a manner analogous to the synthesis of oligonucleotides. In such condensations, the amino and carboxy groups that are not to participate in the reaction can be blocked with protecting groups which are readily introduced, stable to the condensation reactions and selectively removable from the completed peptide. Thus, the overall process generally comprises protection, activation, coupling and deprotection. If a peptide involves amino acids with side chains that may react during condensation, the side chains can also be reversibly protected, removable at the final stage of synthesis.

A successful synthesis for a large polypeptide by a linear strategy must achieve nearly quantitative recoveries for each chemical step. Many automated peptide synthesis schemes take advantage of attachment of the growing polypeptide chain to an insoluble polymer resin support such that the polypeptide can be washed free of byproducts and excess reactants after each reaction step (see for example Merrifield (1963) *J.A.C.S.* 85:2149; Chang et al. (1978) *Int. J. Peptide Protein Res.* 11:246; Barany and Merrifield, *The Peptides*, vol 2 ©1979 NY:Academic Press, pp1–284; Tam, J. P. (1988) *PNAS* 85:5409; and Tam et al. U.S. Pat. No. 4,507,230, incorporated by reference herein). For example, a first amino acid is attached to a resin by a cleavable linkage to its carboxylic group, deblocked at its amino acid side, and coupled with a second activated amino acid carrying a protected α-amino group. The resulting protected dipeptide is deblocked to yield a free amino terminus, and coupled to a third N-protected amino acid. After many repetitions of these steps, the complete polypeptide is cleaved from the resin support and appropriately deprotected.

To generate the set of polypeptide antigens, more than one N-protected amino acid type can be reacted simultaneously in each round of coupling with the growing polypeptide chain to create the desired degenerate amino acid sequence at each amino acid position. In one embodiment, the set of polypeptides will include only those amino acids that are present at any position n in the population of variants above the predetermined threshold frequency.

Alternatively, one can first design the degenerate oligonucleotide, determine the amino acids encoded by the combination of codons and include all the amino acids in the chemical synthesis. For example, a degenerate codon at codon position n, having the sequence MMT and thus coding for either a Thr (ACT), an Asn (AAT), a His (CAT) or a Pro (CCT), can be created at the peptide synthesis level by reacting all four N-protected amino acid types simultaneously with the free amino terminus of the growing, resin-bound peptide. Thus, four subpopulations of peptides will be created, each subpopulation definable by the amino acid type present at the amino acid position n corresponding to the codon position n.

Because the amino acid being added to the resin-bound polypeptide is protected, the growth of the peptide chain is terminated upon addition of the protected amino acid until the subsequent deblocking step. Those skilled in the art will recognize that, due to potential differences in reactivity of various amino acid analogs, it may be desirable to use non-equimolar ratios of amino acid types when simultaneously reacting more than one amino acid type in order to get equimolar ratios of subpopulations. Alternatively, it may be desirable to divide the resin-bound polypeptide into aliquots, each of which is reacted with a distinct amino acid type, the polypeptide products being recombined prior to the next coupling reaction. This technique can be applied to create an amino acid gap in a subpopulation, simply by holding aside an appropriate aliquot during one round of coupling, then recombining all resin-bound polypeptides prior to the next round of coupling. Furthermore, it is apparent that, from the many different blocking and activating groups available, chemical synthesis of the polypeptide can be carried out in either the N-terminal to C-terminal, or C-terminal to N-terminal direction.

The generated set of polypeptide antigens can be covalently or noncovalently modified with non-proteinaceous materials such as lipids or carbohydrates to enhance immunogenecity or solubility. The present invention is understood to include all such chemical modifications of the set of polypeptide antigens so long as the modified peptide antigens retain substantially all the antigenic/immunogenic properties of the parent mixture.

The generated set of polypeptide antigens can also be coupled with or incorporated into a viral particle, a replicating virus, or other microorganism in order to enhance immunogenicity. The set of polypeptide antigens may be chemically attached to the viral particle or microorganism or an immunogenic portion thereof.

There are a large number of chemical cross-linking agents that are known to those skilled in the art. For the present invention, the preferred cross-linking agents are heterobifunctional cross-linkers, which can be used to link proteins in a stepwise manner. Heterobifunctional cross-linkers provide the ability to design more specific coupling methods for conjugating proteins, thereby reducing the occurrences of unwanted side reactions such as homo-protein polymers. A wide variety of heterobifunctional cross-linkers are known in the art. These include: succinimidyl 4-(N-maleimidomethyl)cyclohexane-1-carboxylate (SMCC), m-Maleimidobenzoyl-N-hydroxysuccinimide ester (MBS); N-succinimidyl (4-iodoacetyl)aminobenzoate (SIAB), succinimidyl 4-(p-maleimidophenyl)butyrate (SMPB), 1-ethyl-3-(3-dimethylaminopropyl)carbodiimide hydrochloride (EDC); 4-succinimidyloxycarbonyl-α-methyl-α-(2-pyridyldithio)-tolune (SMPT), N-succinimidyl 3-(2-pyridyldithio)propionate (SPDP), succinimidyl 6-[3-(2-pyridyldithio)propionate]hexanoate (LC-SPDP). Those cross-linking agents having N-hydroxysuccinimide moieties can be obtained as the N-hydroxysulfosuccinimide analogs, which generally have greater water solubility. In addition, those cross-linking agents having disulfide bridges within the linking chain can be synthesized instead as the alkyl derivatives so as to reduce the amount of linker cleavage in vivo.

The introduction of antigen into an animal initiates a series of events culminating in both cellular and humoral immunity. By convention, the property of a molecule that allows it to induce an immune response is called immunogenicity. The property of being able to react with an antibody that has been induced is called antigenicity. Antibodies able to cross-react with two or more different antigens can do so by virtue of some degree of structural and chemical similarity between the antigenic determinants (or "epitopes") of the antigens. A protein immunogen is usually composed of a number of antigenic determinants. Hence, immunizing with a protein results in the formation of antibody molecules with different specificities, the number of different antibodies depending on the number of antigenic determinants and their inherent immunogenicity.

Proteins are highly immunogenic when injected into an animal for whom they are not normal ("self") constituents. Conversely, peptides and other compounds with molecular weights below about 5000 (termed "haptens") daltons, by themselves, do not generally elicit the formation of antibodies. However, if these small molecule antigens are first coupled with a longer immunogenic antigen such as a protein, antibodies can be raised which specifically bind epitopes on the small molecules. Conjugation of haptens to carrier proteins can be carried out as described above.

When necessary, modification of such ligand to prepare an immunogen should take into account the effect on the structural specificity of the antibody. That is, in choosing a site on a ligand for conjugation to a carrier such as protein, the selected site is chosen so that administration of the resulting immunogen will provide antibodies which will recognize the original ligand. Furthermore, not only must the antibody recognize the original ligand, but significant characteristics of the ligand portion of the immunogen must remain so that the antibody produced after administration of the immunogen will more likely distinguish compounds closely related to the ligand which may also be present in the patient sample. In addition, the antibodies should have high binding constants.

Vaccines comprising the generated set of polypeptide antigens, and variants thereof having antigenic properties, can be prepared by procedures well known in the art. For example, such vaccines can be prepared as injectables, e.g., liquid solutions or suspensions. Solid forms for solution in, or suspension in, a liquid prior to injection also can be prepared. Optionally, the preparation also can be emulsified. The active antigenic ingredient or ingredients can be mixed with excipients which are pharmaceutically acceptable and compatible with the active ingredient. Examples of suitable excipients are water, saline, dextrose, glycerol, ethanol, or the like, and combinations thereof. In addition, if desired, the vaccine can contain minor amounts of auxiliary substances such as wetting or emulsifying agents, pH buffering agents, or adjuvants such as aluminum hydroxide or muramyl dipeptide or variations thereof. In the case of peptides, coupling to larger molecules such as Keyhole limpet hemacyanin (KLH) sometimes enhances immunogenicity. The vaccines are conventionally administered parenterally, by injection, for example, either subcutaneously or intramuscularly. Additional formulations which are suitable for other modes of administration include suppositories and, in some cases, oral formulations. For suppositories, the traditional binders and carriers include, for example, polyalkalene glycols or triglycerides. Suppositories can be formed from mixtures containing the active ingredient in the range of about 0.5% to about 10%, preferably about 1% to about 2%. Oral formulations can include such normally employed excipients as, for example, pharmaceutical grades of mannitol, lactose, starch, magnesium stearate, sodium saccharine, cellulose, magnesium carbonate, and the like. These compositions can take the form of solutions, suspensions, tablets, pills, capsules, sustained release formulations or powders and contain from about 10% to about 95% of active ingredient, preferably from about 25% to about 70%.

The active compounds can be formulated into the vaccine as neutral or salt forms. Pharmaceutically acceptable salts include the acid addition salts (formed with the free amino groups of the polypeptides) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like. A vaccine composition may include peptides containing T helper cell epitopes in combination with protein fragments containing the principal neutralizing domain. For instance, several of these epitopes have been mapped within the HIV envelope, and these regions have been shown to stimulate proliferation and lymphokine release from lymphocytes. Providing both of these epitopes in a vaccine comprising a generated set of polypeptide antigens derived from analysis of HIV-1 isolates can result in the stimulation of both the humoral and the cellular immune responses. In addition, commercial carriers and adjuvants are available to enhance immunomodulation of both B-cell and T-cell populations for an immunogen (for example, the IMJECT SUPERCARRIER™ System, Pierce Chemical, Catalog No. 77151G).

Alternatively, a vaccine composition may include a compound which functions to increase the general immune response. One such compound is interleukin-2 (IL-2) which has been reported to enhance immunogenicity by general immune stimulation (Nunberg et al. (1988) *In New Chemical and Genetic Approaches to Vaccination,* Cold Spring Harbor Laboratory, Cold Spring Harbor, N.Y.). IL-2 may be coupled the polypeptides of the generated set of polypeptide antigens to enhance the efficacy of vaccination.

The vaccines are administered in a manner compatible with the dosage formulation, and in such amount as will be therapeutically effective and immunogenic. The quantity to be administered depends on the subject to be treated, capacity of the subjects immune system to synthesize antibodies, and the degree of protection desired. Precise amounts of active ingredient required to be administered depend on the judgment of the practitioner and are peculiar to each individual. Suitable regimes for initial administration and booster shots are also variable, but are typified by an initial administration followed in one or two week intervals by a subsequent injection or other administration.

Antigens that induce tolerance are called toleragens, to be distinguished from immunogens, which generate immunity. Exposure of an individual to immunogenic antigens stimulates specific immunity, and for most immunogenic proteins, subsequent exposures generate enhanced Secondary responses. In contrast, exposure to a toleragenic antigen not only fails to induce specific immunity, but also inhibits lymphocyte activation by subsequent administration of immunogenic forms of the same antigen. Many foreign antigens can be immunogens or toleragens, depending on the physicochemical form, dose, and route of administration. This ability to manipulate responses to antigens can be exploited clinically to augment or suppress specific immunity. For instance, it can be desirable in the context of organ transplant technology to tolerize a transplant recipient with a polypeptide antigen set derived from the frequency analysis of known sub-haplotypes of a class II peptide (i.e., such as the DQ or DR allele products) present on the transplanted tissue in order to minimize rejection. It is also within the equivalence of this invention that the set of polypeptide antigens can be chemically coupled or incorporated as part of a fusion protein with an apoptotic agent, for instance an agent which brings about deregulation of C-myc expression or a cell toxin such as diptheria toxoid, such that programmed cell death is brought about in an antigen specific manner.

Thus it would be routine for one skilled in the art to determine the appropriate administration regimen necessary to induce tolerance to the set of polypeptide antigens of the present invention.

The following example serves to further illustrate the present invention.

EXAMPLE 1

Human Immunodeficiency Virus type I (HIV-1), the causative agent of Acquired Immunodeficiency Syndrome (AIDS), shows very marked sequence diversity between different isolates. The outer envelope glycoprotein gp120 of HIV-1, which facilitates binding of the virion to CD4, has been shown to be the major target of neutralizing antibodies. Studies in humans and mice have revealed a small region of this protein, termed the V3 loop, between Cysteine residues 303 and 338, that evokes the major neutralizing antibodies to the virus. Recombinant or synthetic polypeptides containing V3 loop epitopes of an HIV-1 isolate have been shown to induce relatively high titers of strain-specific neutralizing antibodies. However, even single amino acid substitutions within the V3 loop are sufficient in some cases to greatly reduce antibody binding, in agreement with the strict specificity of neutralizing antibodies to the V3 loop.

Table 3 sets forth the results obtained from frequency analysis of V3-loop sequences of a population of HIV-1 isolates obtained largely from AIDS patients in North America (Wolinsky et al. (1992) *Science* 225:1134; LaRosa et al. (1990) *Science* 249:931; and Holley et al. (1991) *PNAS* 88:6800, incorporated by reference herein). The alignment of each variant sequence is relative to the reference sequence:

```
1         10        20        30        40
|         |         |         |         |
CTRPNNNTRKSIHIGPGRAFY*TTGEIIGDIRQAHC    (SEQ ID NP:NO 5)
``` where cys-1 of the reference sequence corresponds to cys-303 of gp120 according to the nomenclature used herein.

TABLE 3

Frequency Analysis of N. A. Isolates of HIV-1

| V3 Position | Frequency of occurrence (expressed in percent) |
|---|---|
| 1 | C = 100 |
| 2 | T = 86.3; I = 11.3; A = <1; L = <1; M = <1; P = <1; S = <1 |
| 3 | R = 99.4; I = <1; K = <1 |
| 4 | P = 97.3; H = 1.5; L = <1; S = <1 |
| 5 | N = 86.3; S = 7.0; Y = 3.0; G = 1.8; D = <1; H = <1 |
| 6 | N = 90.9; S = 3.4; D = 1.5; Y = 1.2; G = <1; I = <1; K = <1; T = <1 |
| 7 | N = 92.4; T = 3.0; Y = 1.2; D = <1; H = <1; I = <1; K = <1; R = <1 |
| 8 | * = 98.8; I = <2; K = <1 |
| 9 | * = 99.7; K = <1 |
| 10 | T = 92.0; I = 1.8; V = 1.8; A = 1.5; K = <1; R = <1 |
| 11 | R = 88.9; K = 6.3; I = 1.8; E = <1; G = <1; M = <1; P = <1; Q = <1; T = <1 |
| 12 | K = 76.5; R = 17.4; Q = 2.8; N = 2.1; H = <2; E = <1; G = <1 |
| 13 | S = 64.8; G = 21.7; R = 10.6; * = <1; A = <1; ; H = <1; K = <1 |
| 14 | I = 96.1; L = 1.2; E = <1; F = <1; M = <1; T = <1; V = <1 |
| 15 | H = 49.2; N = 9.6; P = 9.0; R = 9.0; T = 8.4; Y = 6.2; S = 5.6; F = 1.5; A = <1; G = <1; K = <1; V = <1 |
| 16 | I = 72.4; M = 18.7; L = 2.0; T = 1.7; F = 1.2; V = 1.2; K = <1; S = <1; R = <1; Y = <1 |
| 17 | * = 97.3; Q = 2.5; R = <1 |
| 18 | * = 97.3; R = 2.5; G = <1 |
| 19 | G = 90.6; M = 7.4; A = <1; E = <1; I = <1; ; R = <1; T = <1 |
| 20 | P = 88.9; G = 7.9; L = 1.2; A = <1; Q = <1; S = <1 |
| 21 | G = 99.0; E = <1; R = <1 |
| 22 | R = 80.1; K = 11.9; S = 3.7; Q = 2.5; * = <1; G = <1; M = <1 |
| 23 | A = 86.0; V = 4.4; T = 4.2; K = 1.5; R = 1.5; N = 1.2; P = <1; S = <1; W = <1 |
| 24 | F = 75.9; W = 8.1; I = 7.1; V = 3.4; L = 2.5; Y = 1.7; S = <1; T = <1 |
| 25 | Y = 84.0; H = 6.4; V = 4.2; L = 2.0; F = 1.2; I = <1; M = <1; N = <1; R = <1 |
| 26 | * = 99.4; H = <1; T = <1 |
| 27 | A = 52.4; T = 43.9; V = 1.8; * = <1; Q = <1; S = <1; Y = <1 |
| 28 | T = 88.4; I = 3.7; R = 2.7; A = 2.4; Q = 1.2; K = <1; M = <1, P = <1; Y = <1 |
| 29 | G = 76.8; N = 4.9; E = 4.9; T = 2.7; H = 2.1; K = 1.8; R = 1.8; D = 1.2; A = <1; I = <1; P = <1; Q = <1; * = <1 |
| 30 | E = 30.8; D = 23.8; R = 9.82; K = 8.2; * = 7.6; Q = 7.9; N = 3.4; G = 2.7; A = <1; I = <1; S = <1; T = <1 |
| 31 | I = 87.5; F = 7.6; V = 2.7; L = <1; K = <1; M = <1; R = <1 |
| 32 | I = 77.7; V = 8.8; T = 6.1; * = 87.5; Q = 1.2; R = <2; A = <1; E = <1; G = <1; K = <1; L = <1; M = <1 |
| 33 | G = 96.6; E = 1.2; A = <1; K = <1; N = <1; R = <1; S = <1 |
| 34 | D = 84.2; N = 16.4; G = <1; I = <1; M = <1; R = <1; T = <1 |
| 35 | I = 92.1; M = 4.6; F = 2.1; E = <1; L = <1; T = <1 |

TABLE 3-continued

Frequency Analysis of N. A. Isolates of HIV-1

| V3 Position | Frequency of occurrence (expressed in percent) |
|---|---|
| 36 | R = 96.9; * = <1; E = <1; G = <1; K = <1; S = <1; C = <1 |
| 37 | Q = 82.6; K = 11.9; R = 3.5 |
| 38 | A = 100 |
| 39 | H = 90.6; Y = 4.5; R = 3.3; Q = 1.6 |
| 40 | C = 99.2; Y = <1 |

(* represents an amino acid gap)

From the frequency of occurrence data calculated in Table 3, we have determined the most commonly occurring amino acid types at each position which are collectively represented in at least 90% of the variants analyzed. The corresponding degenerate codon was selected for each of the amino acid positions and used to determine a degenerate oligonucleotide sequence, which includes the codons for 10 amino acid residues flanking the V3 loop sequences on either side, represented by the general sequence:

5'-GTTCAGCTGAACGAATCTGTTGACATCAACTG
CAYCCGTCCGARCAACAACACCARAARARGM
ATCMVCATSGGCCCGGGCARAGYTWTCYA
CRCTAYCSRGSRMWTCRYTGGTRACATCCGTM
AGGCTCACTGCAACATCTCTCGTGCTAAATGG
AACAACACT-3' (SEQ ID NO:6)

This degenerate nucleotide code is for polypeptide antigens represented by the general sequence:

Val Gln Leu Asn Glu Ser Val Glu Ile Asn Cys $Xaa_1$ Arg Pro $Xaa_2$ Asn Asn Thr $Xaa_3$ $Xaa_4$ $Xaa_5$ Ile $Xaa_6$ $Xaa_7$ Gly Pro Gly $Xaa_8$ $Xaa_9$ $Xaa_{10}$ $Xaa_{11}$ $Xaa_{12}$ $Xaa_{13}$ $Xaa_{14}$ $Xaa_{15}$ $Xaa_{16}$ $Xaa_{17}$ Gly $Xaa_{18}$ Ile Arg $Xaa_{19}$ Ala His Cys Asn Ile Ser Arg Ala Lys Trp Asn Asn Thr (SEQ ID NO: 7)

where $Xaa_1$ is selected from the group consisting of Thr and Ile;

$Xaa_2$ is selected from the group consisting of Asn and Ser;

$Xaa_3$ is selected from the group consisting of Arg and Lys;

$Xaa_4$ is selected from the group consisting of Arg and Lys;

$Xaa_5$ is selected from the group consisting of Arg, Gly and Ser;

$Xaa_6$ is selected from the group consisting of Asn, Pro, Ser, Arg, Thr and His;

$Xaa_7$ is selected from the group consisting of Met and Ile;

$Xaa_8$ is selected from the group consisting of Lys and Arg:

$Xaa_9$ is selected from the group consisting of Val and Ala;

$Xaa_{10}$ is selected from the group consisting of Ile and Phe;

$Xaa_{11}$ is selected from the group consisting of His and Tyr;

$Xaa_{12}$ is selected from the group consisting of Ala and Thr;

$Xaa_{13}$ is selected from the group consisting of Ile and Thr;

$Xaa_{14}$ is selected from the group consisting of Arg, Asn, Glu and Gly;

$Xaa_{15}$ is selected from the group consisting of Gly, Arg, His, Gln, Asp and Glu;

$Xaa_{16}$ is selected from the group consisting of Phe and Ile;

$Xaa_{17}$ is selected from the group consisting of Ala, Thr, Val and Ile;

$Xaa_{18}$ is selected from the group consisting of Asn and Asp;

$Xaa_{19}$ is selected from the group consisting of Lys and Gln.

As described above, the degenerate oligonucleotide can be enzymatically ligated with the appropriate DNA sequences to create a gene library which codes for proteins comprising the polypeptide antigen set.

Likewise, FIG. 2 illustrates the results of a selection criteria comprising the determination of the most commonly occurring amino acid types at each position which are collectively represented in at least 80% of the variants analyzed. In this instance, the degenerate oligonucleotide sequence determined is represented by the general sequence:

5'-GTT CAG CTG AAC GAA TCT GTT GAC ATC AAC
TGC ACC CGT CCG AAC AAC AAC ACC CGT ARA
RGC ATC MVC ATS GGC CCG GCC CGT GCT WTC
TAC RCT ACC GRG SRM ATC RTT GGT GAC ATC
CGT CAG GCT CAC TGC AAC ATC TCT CGT GCT
AAA TGG AAC AAC ACT-3' (SEQ ID NO:8)

and corresponds to the polypeptide antigen set represented by the following general sequence:

Val Gln Leu Asn Glu Ser Val Glu Ile Asn Cys Thr Arg Pro Asn Asn Asn Thr Arg $Xaa_1$ $Xaa_2$ Ile $Xaa_3$ $Xaa_4$ Gly Pro Gly Arg Ala $Xaa_5$ Tyr $Xaa_6$ Thr $Xaa_7$ $Xaa_8$ Ile $Xaa_9$ Gly Asp Ile Arg Gln Ala His Cys Asn Ile Ser Arg Ala Lys Trp Asn Asn Thr (SEQ ID NO:9)

where $Xaa_1$ is selected from the group consisting of Lys and Arg;

$Xaa_2$ is selected from the group consisting of Ser and Gly;

$Xaa_3$ is selected from the group consisting of His, Arg, Pro, Thr and Asn;

$Xaa_4$ is selected from the group consisting of Ile and Met;

$Xaa_5$ is selected from the group consisting of Phe and Ile;

$Xaa_6$ is selected from the group consisting of Thr and Ala;

$Xaa_7$ is selected from the group consisting of Gly and Glu;

$Xaa_8$ is selected from the group consisting of Glu, Asp, Arg, Lys and Gln;

$Xaa_9$ is selected from the group consisting of Ile and Val.

When the population of HIV-1 V3 loop variants analyzed was selected so as to include sequences from HIV-1 isolates of Ugandan origin (Oram et al. (1991) *AIDS Research and Human Retroviruses* 7:605, incorporated by reference herein), the following degenerate oligonucleotide sequence was determined;

5'-GTTCAGCTGAACGAATCTGTTGACATCAACTG
CWCCCGTCCGWACAAMAASAYCAKAMA
GRGMMTSMVCMTSGGCCCGGGCMRAGY
TDTSYWCACTACCRRAADAAYCGGCKACATC
SGTCAGGCTYACTGCAACATCTCTCGTGCTAA
ATGGAACAACACT-3' (SEQ ID NO:10)

This set codes for following polypeptide antigen set given by the general formula:

Val Gln Leu Asn Glu Ser Val Glu Ile Asn Cys $Xaa_1$ Arg Pro $Xaa_2$ $Xaa_3$ $Xaa_4$ $Xaa_5$ $Xaa_6$ $Xaa_7$ $Xaa_8$ $Xaa_9$ $Xaa_{10}$ $Xaa_{11}$ Gly Pro Gly $Xaa_{12}$ $Xaa_{13}$ $Xaa_{14}$ $Xaa_{15}$ Thr Thr $Xaa_{16}$ $Xaa_{17}$ $Xaa_{18}$ Gly $Xaa_{19}$ Ile $Xaa_{20}$ Gln Ala $Xaa_{21}$ Cys Asn Ile Ser Arg Ala Lys Trp Asn Asn Thr (SEQ ID NO:11)

where $Xaa_1$ is selected from the group consisting of Thr and Ser;

$Xaa_2$ is selected from the group consisting of Asn and Tyr;

$Xaa_3$ is selected from the group consisting of Asn and Lys;

$Xaa_4$ is selected from the group consisting of Asn and Lys;

$Xaa_5$ is selected from the group consisting of Thr and Ile;

$Xaa_6$ is selected from the group consisting of Arg and Ile;

$Xaa_7$ is selected from the group consisting of Lys and Gln;

$Xaa_8$ is selected from the group consisting of Ser, Gly and Arg;

$Xaa_9$ is selected from the group consisting of Ile, Met and Leu;

$Xaa_{10}$ is selected from the group consisting of His, Asn, Arg, Ser, Pro and Thr;

$Xaa_{11}$ is selected from the group consisting of Ile, Met, and Leu;

$Xaa_{12}$ is selected from the group consisting of Arg, Lys, and Gln;

$Xaa_{13}$ is selected from the group consisting of Ala and Val;

$Xaa_{14}$ is selected from the group consisting of Phe, Leu, Ile, Met and Val;

$Xaa_{15}$ is selected from the group consisting of Tyr, Phe, His and Leu;

$Xaa_{16}$ is selected from the group consisting of Gly, Lys, Arg and Glu;

Xaa17 is selected from the group consisting of Ile, Lys and Arg;

$Xaa_{18}$ is selected from the group consisting of Ile and Thr;

$Xaa_{19}$ is selected from the group consisting of Asp and Tyr;

$Xaa_{20}$ is selected from the group consisting of Arg and Gly;

$Xaa_{21}$ is selected from the group consisting of His and Tyr.

To synthesize this degenerate oligonucleotide sequence, the following synthetic oligonucleotides were produced.

These oligonucleotides were assembled as follows, $$5'\underline{\quad CR11 \quad}3' \quad 5'\underline{\quad 920465 \quad}3' \quad 5'\underline{\quad CR23 \quad}3'$$
$$3'\underline{\quad CR22 \quad}5' \quad 3'\underline{\quad 920466 \quad}5' \quad 3'\underline{\quad CR12 \quad}5'$$

Stock solutions of each of the above oligonucleotides were made by dissolving the oligonucleotide in sterile water. Aliquots of the stock solutions were kinased, then mixed together for annealing in klenow buffer and sterile water. The reaction mixture was heated to 94° C. and slowly cooled at 1° C. per 15 seconds. To the reaction mixture was then added dGTP, dCTP, dTTP, dATP, klenow, ATP and ligase. The mixture was incubated at room temperature over night. The mixture was then precipitated with 95% ethanol and the DNA pellet was washed with 70% ethanol, dried and dissolved in 20 microliters of sterile water.

The isolated DNA sequences were then PCR amplified using CR11 and CR12 as the 5' and 3' amplimers respectively. The 5' amplimer has EcoRI, NcoI and PvuII sites and the 3' amplimer has a SalI site which allows for cloning into several expression systems.

The PCR products were isolated upon gel electrophoresis, cleaned with "Gene clean" (Bio101) and cut with EcoRI and SalI restriction enzymes. The restricted DNA library was then cloned in pFLAG plasmid (IBI FLAG Biosystem, Catalogue Number: IB 13000) treated with EcoRI and SalI and with calf intestinal phosphatase. The library of vectors so produced codes for an in-frame fusion of FLAG peptide gene and V3 gene variants. Upon induction with IPTG, a library of fusion polypeptides composed of the FLAG peptide (amino-terminus) and V3 loop variants (carboxy-terminus) was produced.

The PCR products (V3 loop gene library) can also be cut with PvuII and SalI and ligated into either pEZZmp18 or pEBBmp18 expression system (Stahl et al. (1989) *J. Immunol. Meth.* 124:43, incorporated by reference herein) to create a library of fusion proteins comprising a staphylococcal protein and the V3 sequences. All three plasmids contain the pBR322 ori to drive replication in the appropriate host organism and F1 ori to facilitate site directed mutagenesis.

The set of polypeptide antigens can be used to raise polyclonal sera in rabbits by standard immunization procedures, and a polyclonal antibody mixture purified. HIV infectivity and gp120/CD4 binding assays can be used to test the effectiveness of the set of polypeptide antigen in eliciting an immune response (e.g., antibody response) against variant of HIV.

The polyclonal sera can also be used to artificially apply selective mutational pressure on the virus, in order to

```
#CR11    (SEQ ID NO:12)    5' -CGCGAATTCTCCATGGTTCAGCTGAACGAATCTGTTGAC3'

#CR22    (SEQ ID NO:13)    5' -CGGACGGGWGCAGTTGATGTCAACAGATTCGTTCA

#920465  (SEQ ID NO:14)    5' -ATCAACTGCWCCCGTCCGWACAAMAASAYCAKAMAGRGMM
                               TSMVCMTSGGCCCGG

#920466  (SEQ ID NO:15)    5' -ATGTTGCAGTRAGCCTGACSGATGTMGCCGRTTHTTYYGG
                               TAGTGWRSAHARCTYKACCCGGGCCSAKG

#CR23    (SEQ ID NO:16)    5' -CAGGCTYACTGCAACATCTCTCGTGCTAAATGGAACA

#CR12    (SEQ ID NO:17)    5' -CGCGTCGACAGTGTTGTTCCATTTAGCACGAGAG3'
``` compress the evolutionary timetable. For instance, HIV-infected cells which are able to mutate in a manner which allows the new variant to escape recognition by the polyclonal sera can be scored for. These variants will be sequenced, and incorporated into a population analysis in a weighted manner so as to be included in a subsequent set of polypeptide antigens.

Equivalents

Those skilled in the art will recognize, or be able to ascertain using no more than routine experimentation, numerous equivalents to the specific procedures described herein. Such equivalents are considered to be within the scope of this invention and are covered by the following claims.

---

What is claimed is:

1. A method of producing a set of polypeptides having amino acid sequences derived from a population of variants of a pathogen protein, or antigenic portion thereof, comprising the steps of:
   a. selecting a protein of a pathogen, or antigenic portion thereof, which exhibits a population of variants;
   b. determining the number of times each type of amino acid occurs at each amino acid position in the variants;
   c. calculating the frequency of occurrence of each type of amino acid at each amino acid position in the variants;
   d. synthesizing a set of polypeptides wherein the set of polypeptides consists of polypeptides wherein each amino acid at each position of the polypeptide occurs in greater than a selected frequency when compared to the corresponding amino acids of all of the variants, each polypeptide within the set being from 8 to 150 amino acids in length; and
   e. collecting the set of polypeptides following synthesis.

2. The method according to claim 1, wherein each amino acid type at each amino acid position of the set occurs at greater than a 5% frequency at the corresponding amino acid position in the variants.

3. The method according to claim 1, wherein each amino acid type at each amino acid position of the set occurs at greater than a 10% frequency at the corresponding amino acid position in the variants.

4. The method according to claim 1, wherein each amino acid type at each amino acid position of the set occurs at greater than a 15% frequency at the corresponding amino acid position in the variants.

5. The method according to claim 1, wherein the set of polypeptides is produced by i) synthesizing a degenerate oligonucleotide sequence having a minimum number of nucleotide combinations at each codon position which combinations include the codons coding for each type of amino acid at each amino acid position of the set; and
ii) expressing the degenerate oligonucleotide in an expression system to produce the set of polypeptides.

6. The method according to claim 1, wherein the set of polypeptides is synthesized by organo-chemical peptide synthesis.

7. A set of polypeptides wherein the set of polypeptides consists of polypeptides which consist of the amino acid sequence:

Val Gln Leu Asn Glu Ser Val Glu Ile Asn Cys $Xaa_1$ Arg Pro $Xaa_2$ $Xaa_3$ $Xaa_4$ $Xaa_5$ $Xaa_6$ $Xaa_7$ $Xaa_8$ $Xaa_9$ $Xaa_{10}$ $Xaa_{11}$ Gly Pro Gly $Xaa_{12}$ $Xaa_{13}$ $Xaa_{14}$ $Xaa_{15}$ Thr Thr $Xaa_{16}$ $Xaa_{17}$ $Xaa_{18}$ Gly $Xaa_{19}$ Ile $Xaa_{20}$ Gln Ala $Xaa_{21}$ Cys Asn Ile Ser Arg Ala Lys Trp Asn Asn Thr (SEQ ID NO: 11)

where $Xaa_1$ is selected from the group consisting of Thr and Ser;

$Xaa_2$ is selected from the group consisting of Asn and Tyr;

$Xaa_3$ is selected from the group consisting of Asn and Lys;

$Xaa_4$ is selected from the group consisting of Asn and Lys;

$Xaa_5$ is selected from the group consisting of Thr and Ile;

$Xaa_6$ is selected from the group consisting of Arg and Ile;

$Xaa_7$ is selected from the group consisting of Lys and Gln;

$Xaa_8$ is selected from the group consisting of Ser, Gly and Arg;

$Xaa_9$ is selected from the group consisting of Ile, Met and Leu;

$Xaa_{10}$ is selected from the group consisting of His, Asn, Arg, Ser, Pro and Thr;

$Xaa_{11}$ is selected from the group consisting of Ile, Met, and Leu;

$Xaa_{12}$ is selected from the group consisting of Arg, Lys, and Gln;

$Xaa_{13}$ is selected from the group consisting of Ala and Val;

$Xaa_{14}$ is selected from the group consisting of Phe, Leu, Ile, Met and Val;

$Xaa_{15}$ is selected from the group consisting of Tyr, Phe, His and Leu;

$Xaa_{16}$ is selected from the group consisting of Gly, Lys, Arg and Glu;

$Xaa_{17}$ is selected from the group consisting of Ile, Lys and Arg;

$Xaa_{18}$ is selected from the group consisting of Ile and Thr;

$Xaa_{19}$ is selected from the group consisting of Asp and Tyr;

$Xaa_{20}$ is selected from the group consisting of Arg and Gly; and $Xaa_{21}$ is selected from the group consisting of His and Tyr.

8. A composition comprising the set of polypeptides of claim 7 and a physiological vehicle.

9. A set of polypeptides wherein the set of polypeptides consists of polypeptides which consist of the amino acid sequence:

Val Gln Leu Asn Glu Ser Val Glu Ile Asn Cys $Xaa_1$ Arg Pro $Xaa_2$ Asn Asn Thr $Xaa_3$ $Xaa_4$ $Xaa_5$ Ile $Xaa_6$ $Xaa_7$ Gly Pro Gly $Xaa_8$ $Xaa_9$ $Xaa_{10}$ $Xaa_{11}$ $Xaa_{12}$ $Xaa_{13}$ $Xaa_{14}$ $Xaa_{15}$ $Xaa_{16}$ $Xaa_{17}$ Gly $Xaa_{18}$ Ile Arg $Xaa_{19}$ Ala His Cys Asn Ile Ser Arg Ala Lys Trp Asn Asn Thr (SEQ ID NO: 7)

where $Xaa_1$ is selected from the group consisting of Thr and Ile;

$Xaa_2$ is selected from the group consisting of Asn and Ser;

$Xaa_3$ is selected from the group consisting of Arg and Lys;

$Xaa_4$ is selected from the group consisting of Arg and Lys;

$Xaa_5$ is selected from the group consisting of Arg, Gly and Ser;

$Xaa_6$ is selected from the group consisting of Asn, Pro, Ser, Arg, Thr and His;

$Xaa_7$ is selected from the group consisting of Met and Ile;

$Xaa_8$ is selected from the group consisting of Lys and Arg;

$Xaa_9$ is selected from the group consisting of Val and Ala;

$Xaa_{10}$ is selected from the group consisting of Ile and Phe;

$Xaa_{11}$ is selected from the group consisting of His and Thr;

$Xaa_{12}$ is selected from the group consisting of Ala and Thr;

$Xaa_{13}$ is selected from the group consisting of Ile and The;

$Xaa_{14}$ is selected from the group consisting of Arg, Asn, His, Gln, Asp and Glu;

$Xaa_{15}$ is selected from the group consisting of Gly, Arg, His, Gln, Asp and Glu;

$Xaa_{16}$ is selected from the group consisting of Phe and Ile;

$Xaa_{17}$ is selected from the group consisting of Ala, Thr, Val and Ile;

$Xaa_{18}$ is selected from the group consisting of Asn and Asp; and $Xaa_{19}$ is selected from the group consisting of Lys and Gln.

10. A composition comprising the set of polypeptides of claim 9 and a physiological vehicle.

11. A set of polypeptides wherein the set of polypeptides consists of polypeptides which consist of the amino acid sequence:

Val Gln Leu Asn Glu Ser Val Glu Ile Asn Cys Thr Arg Pro Asn Asn Asn Thr Arg $Xaa_1$ $Xaa_2$ Ile $Xaa_3$ $Xaa_4$ Gly Pro Gly Arg Ala $Xaa_5$ Tyr $Xaa_6$ Thr $Xaa_7$ $Xaa_8$ Ile $Xaa_9$ Gly Asp Ile Arg Gln Ala His Cys Asn Ile Ser Arg Ala Lys Trp Asn Asn Thr (SEQ ID NO: 11)

$Xaa_1$ is selected from the group consisting of Lys and Arg;

$Xaa_2$ is selected from the group consisting of Ser and Gly;

$Xaa_3$ is selected from the group consisting of His, Arg, Pro, Thr and Asn;

$Xaa_4$ is selected from the group consisting of Ile and Met;

$Xaa_5$ is selected from the group consisting of Phe and Ile;

$Xaa_6$ is selected from the group consisting of Thr and Ala;

Xaa$_7$ is selected from the group consisting of Gly and Glu;

Xaa$_8$ is selected from the group consisting of Glu, Asp, Arg, Lys and Gln; and Xaa$_9$ is selected from the group consisting of Ile and Val.

12. A composition comprising the set of polypeptides of claim 11 and a physiological vehicle.

13. A method of producing a set of polypeptides having amino acid sequences derived from a population of variants of a pathogen protein, or antigenic portion thereof, comprising the steps of:

a. selecting a protein of a pathogen, or antigenic portion thereof, which exhibits a population of variants;

b. determining the number of times each type of amino acid occurs at each amino acid position in the variants;

c. calculating the frequency of occurrence of each type of amino acid at each amino acid position in the variants;

d. synthesizing a set of polypeptides wherein the set of polypeptides consists of polypeptides wherein each amino acid at each position of the polypeptide occurs in greater than a selected frequency when compared to the corresponding amino acids of all of the variants, each polypeptide within the set being from 55 to 150 amino acids in length; and e. collecting the set of polypeptides following synthesis.

* * * * *

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
      (A) LENGTH: 35 amino acids
      (B) TYPE: amino acid
      (D) TOPOLOGY: linear (ii) MOLECULE TYPE: peptide (v) FRAGMENT TYPE: internal (xi) SEQUENCE DESCRIPTION: SEQ ID NO:1:

```
Cys Thr Arg Pro Asn Asn Asn Thr Arg Lys Ser Ile His Ile Gly Pro
1               5                   10                  15

Gly Arg Ala Leu Tyr Thr Thr Gly Glu Ile Ile Gly Asp Ile Arg Gln
            20                  25                  30

Ala His Cys
        35
```

(2) INFORMATION FOR SEQ ID NO:2:

(i) SEQUENCE CHARACTERISTICS:
      (A) LENGTH: 36 amino acids
      (B) TYPE: amino acid
      (D) TOPOLOGY: linear (ii) MOLECULE TYPE: peptide (v) FRAGMENT TYPE: internal (xi) SEQUENCE DESCRIPTION: SEQ ID NO:2:

```
Cys Thr Arg Pro Asn Asn Asn Thr Arg Lys Lys Ile Arg Ile Gln Arg
1               5                   10                  15

Gly Pro Gly Arg Ala Phe Val Thr Ile Gly Lys Ile Gly Asn Met Arg
            20                  25                  30

Gln Ala His Cys
        35
```

(2) INFORMATION FOR SEQ ID NO:3:

(i) SEQUENCE CHARACTERISTICS:
      (A) LENGTH: 35 amino acids
      (B) TYPE: amino acid
      (D) TOPOLOGY: linear (ii) MOLECULE TYPE: peptide (v) FRAGMENT TYPE: internal (xi) SEQUENCE DESCRIPTION: SEQ ID NO:3:

```
Cys Thr Arg Pro Asn Asn Asn Thr Arg Lys Ser Ile Thr Ile Gly Pro
1               5                   10                  15
```

```
Gly Arg Ala Phe Tyr Ala Thr Gly Asp Ile Ile Gly Asp Ile Arg Gln
            20                  25                  30

Ala His Cys
        35
```

(2) INFORMATION FOR SEQ ID NO:4:

(i) SEQUENCE CHARACTERISTICS:
        (A) LENGTH: 34 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:4:

```
Cys Thr Arg Pro Asn Asn Asn Thr Arg Lys Lys Ile Arg Ile Gly Pro
1               5                  10                  15

Gly Arg Ala Phe Val Thr Ile Gly Lys Ile Gly Asn Met Arg Gln Ala
            20                  25                  30

His Cys
```

(2) INFORMATION FOR SEQ ID NO:5:

(i) SEQUENCE CHARACTERISTICS:
        (A) LENGTH: 35 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:5:

```
Cys Thr Arg Pro Asn Asn Asn Thr Arg Lys Ser Ile His Ile Gly Pro
1               5                  10                  15

Gly Arg Ala Phe Tyr Thr Thr Gly Glu Ile Ile Gly Asp Ile Arg Gln
            20                  25                  30

Ala His Cys
        35
```

(2) INFORMATION FOR SEQ ID NO:6:

(i) SEQUENCE CHARACTERISTICS:
        (A) LENGTH: 165 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

```
GTTCAGCTGA ACGAATCTGT TGACATCAAC TGCAYCCGTC CGARCAACAA CACCARAARA      60

RGMATCMVCA TSGGCCCGGG CARAGYTWTC YACRCTAYCS RGSRMWTCRY TGGTRACATC     120

CGTMAGGCTC ACTGCAACAT CTCTCGTGCT AAATGGAACA ACACT                    165
```

(2) INFORMATION FOR SEQ ID NO:7:

(i) SEQUENCE CHARACTERISTICS:
        (A) LENGTH: 55 amino acids
        (B) TYPE: amino acid
        (D) TOPOLOGY: linear

```
   (ii) MOLECULE TYPE: peptide (v) FRAGMENT TYPE: internal (ix) FEATURE:
        (A) NAME/KEY: Modified-site
        (B) LOCATION: 12
        (D) OTHER INFORMATION: /note= "Xaa is Thr or Ile"

(ix) FEATURE:
        (A) NAME/KEY: Modified-site
        (B) LOCATION: 15
        (D) OTHER INFORMATION: /note= "Xaa is Asn or Ser"

(ix) FEATURE:
        (A) NAME/KEY: Modified-site
        (B) LOCATION: 19
        (D) OTHER INFORMATION: /note= "Xaa is Arg or Lys"

(ix) FEATURE:
        (A) NAME/KEY: Modified-site
        (B) LOCATION: 20
        (D) OTHER INFORMATION: /note= "Xaa is Arg or Lys"

(ix) FEATURE:
        (A) NAME/KEY: Modified-site
        (B) LOCATION: 21
        (D) OTHER INFORMATION: /note= "Xaa is Arg, Gly or Ser"

(ix) FEATURE:
        (A) NAME/KEY: Modified-site
        (B) LOCATION: 23
        (D) OTHER INFORMATION: /note= "Xaa is Asn, Pro, Ser, Arg,
            Thr or His"

(ix) FEATURE:
        (A) NAME/KEY: Modified-site
        (B) LOCATION: 24
        (D) OTHER INFORMATION: /note= "Xaa is Met or Ile"

(ix) FEATURE:
        (A) NAME/KEY: Modified-site
        (B) LOCATION: 28
        (D) OTHER INFORMATION: /note= "Xaa is Lys or Arg"

(ix) FEATURE:
        (A) NAME/KEY: Modified-site
        (B) LOCATION: 29
        (D) OTHER INFORMATION: /note= "Xaa is Val or Ala"

(ix) FEATURE:
        (A) NAME/KEY: Modified-site
        (B) LOCATION: 30
        (D) OTHER INFORMATION: /note= "Xaa is Ile or Phe"

(ix) FEATURE:
        (A) NAME/KEY: Modified-site
        (B) LOCATION: 31
        (D) OTHER INFORMATION: /note= "Xaa is His or Tyr"

(ix) FEATURE:
        (A) NAME/KEY: Modified-site
        (B) LOCATION: 32
        (D) OTHER INFORMATION: /note= "Xaa is Ala or Thr"

(ix) FEATURE:
        (A) NAME/KEY: Modified-site
        (B) LOCATION: 33
        (D) OTHER INFORMATION: /note= "Xaa is Ile or Thr"

(ix) FEATURE:
        (A) NAME/KEY: Modified-site
        (B) LOCATION: 34
        (D) OTHER INFORMATION: /note= "Xaa is Arg, Asn, Glu or Gly"

(ix) FEATURE:
        (A) NAME/KEY: Modified-site
        (B) LOCATION: 35
        (D) OTHER INFORMATION: /note= "Xaa is Gly, Arg, His, Gln,
```

```
                 Asp or Glu"

(ix) FEATURE:
         (A) NAME/KEY: Modified-site
         (B) LOCATION: 36
         (D) OTHER INFORMATION: /note= "Xaa is Phe or Ile"

(ix) FEATURE:
         (A) NAME/KEY: Modified-site
         (B) LOCATION: 37
         (D) OTHER INFORMATION: /note= "Xaa is Ala, Thr, Val or Ile"

(ix) FEATURE:
         (A) NAME/KEY: Modified-site
         (B) LOCATION: 39
         (D) OTHER INFORMATION: /note= "Xaa is Asn or Asp"

(ix) FEATURE:
         (A) NAME/KEY: Modified-site
         (B) LOCATION: 42
         (D) OTHER INFORMATION: /note= "Xaa is Lys or Gln"

(xi) SEQUENCE DESCRIPTION: SEQ ID NO:7:

Val Gln Leu Asn Glu Ser Val Glu Ile Asn Cys Xaa Arg Pro Xaa Asn
1               5                  10                  15

Asn Thr Xaa Xaa Xaa Ile Xaa Xaa Gly Pro Gly Xaa Xaa Xaa Xaa Xaa
            20                  25                  30

Xaa Xaa Xaa Xaa Xaa Gly Xaa Ile Arg Xaa Ala His Cys Asn Ile Ser
        35                  40                  45

Arg Ala Lys Trp Asn Asn Thr
    50                  55

(2) INFORMATION FOR SEQ ID NO:8:

(i) SEQUENCE CHARACTERISTICS:
        (A) LENGTH: 165 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

GTTCAGCTGA ACGAATCTGT TGACATCAAC TGCACCCGTC CGAACAACAA CACCCGTARA       60

RGCATCMVCA TSGGCCCGGC CCGTGCTWTC TACRCTACCG RGSRMATCRT TGGTGACATC      120

CGTCAGGCTC ACTGCAACAT CTCTCGTGCT AAATGGAACA ACACT                     165

(2) INFORMATION FOR SEQ ID NO:9:

(i) SEQUENCE CHARACTERISTICS:
        (A) LENGTH: 55 amino acids
        (B) TYPE: amino acid
        (D) TOPOLOGY: linear (ii) MOLECULE TYPE: peptide (v) FRAGMENT TYPE: internal (ix) FEATURE:
        (A) NAME/KEY: Modified-site
        (B) LOCATION: 20
        (D) OTHER INFORMATION: /note= "Xaa is Lys or Arg"

(ix) FEATURE:
        (A) NAME/KEY: Modified-site
        (B) LOCATION: 21
        (D) OTHER INFORMATION: /note= "Xaa is Ser or Gly"

(ix) FEATURE:
        (A) NAME/KEY: Modified-site
```

(B) LOCATION: 23
    (D) OTHER INFORMATION: /note= "Xaa is His, Arg, Pro, Thr
        or Asn"

(ix) FEATURE:
    (A) NAME/KEY: Modified-site
    (B) LOCATION: 24
    (D) OTHER INFORMATION: /note= "Xaa is Ile or Met"

(ix) FEATURE:
    (A) NAME/KEY: Modified-site
    (B) LOCATION: 30
    (D) OTHER INFORMATION: /note= "Xaa is Phe or Ile"

(ix) FEATURE:
    (A) NAME/KEY: Modified-site
    (B) LOCATION: 32
    (D) OTHER INFORMATION: /note= "Xaa is Tre or Ala"

(ix) FEATURE:
    (A) NAME/KEY: Modified-site
    (B) LOCATION: 34
    (D) OTHER INFORMATION: /note= "Xaa is Gly or Glu"

(ix) FEATURE:
    (A) NAME/KEY: Modified-site
    (B) LOCATION: 35
    (D) OTHER INFORMATION: /note= "Xaa is Glu, Asp, Arg, Lys
        or Gln"

(ix) FEATURE:
    (A) NAME/KEY: Modified-site
    (B) LOCATION: 37
    (D) OTHER INFORMATION: /note= "Xaa is Ile or Val"

(xi) SEQUENCE DESCRIPTION: SEQ ID NO:9:

Val Gln Leu Asn Glu Ser Val Glu Ile Asn Cys Thr Arg Pro Asn Asn
1               5                   10                  15

Asn Thr Arg Xaa Xaa Ile Xaa Xaa Gly Pro Gly Arg Ala Xaa Tyr Xaa
            20                  25                  30

Thr Xaa Xaa Ile Xaa Gly Asp Ile Arg Gln Ala His Cys Asn Ile Ser
        35                  40                  45

Arg Ala Lys Trp Asn Asn Thr
    50                  55

(2) INFORMATION FOR SEQ ID NO:10:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

GTTCAGCTGA ACGAATCTGT TGACATCAAC TGCWCCCGTC CGWACAAMAA SAYCAKAMAG      60

RGMMTSMVCM TSGGCCCGGG CMRAGYTDTS YWCACTACCR RAADAAYCGG CKACATCSGT     120

CAGGCTYACT GCAACATCTC TCGTGCTAAA TGGAACAACA CT                        162

(2) INFORMATION FOR SEQ ID NO:11:

(i) SEQUENCE CHARACTERISTICS:
        (A) LENGTH: 54 amino acids
        (B) TYPE: amino acid
        (D) TOPOLOGY: linear (ii) MOLECULE TYPE: peptide (v) FRAGMENT TYPE: internal

```
(ix) FEATURE:
     (A) NAME/KEY: Modified-site
     (B) LOCATION: 12
     (D) OTHER INFORMATION: /note= "Xaa is Thr or Ser"

(ix) FEATURE:
     (A) NAME/KEY: Modified-site
     (B) LOCATION: 15
     (D) OTHER INFORMATION: /note= "Xaa is Asn or Tyr"

(ix) FEATURE:
     (A) NAME/KEY: Modified-site
     (B) LOCATION: 16
     (D) OTHER INFORMATION: /note= "Xaa is Asn or Lys"

(ix) FEATURE:
     (A) NAME/KEY: Modified-site
     (B) LOCATION: 17
     (D) OTHER INFORMATION: /note= "Xaa is Asn or Lys"

(ix) FEATURE:
     (A) NAME/KEY: Modified-site
     (B) LOCATION: 18
     (D) OTHER INFORMATION: /note= "Xaa is Thr or Ile"

(ix) FEATURE:
     (A) NAME/KEY: Modified-site
     (B) LOCATION: 19
     (D) OTHER INFORMATION: /note= "Xaa is Arg or Ile"

(ix) FEATURE:
     (A) NAME/KEY: Modified-site
     (B) LOCATION: 20
     (D) OTHER INFORMATION: /note= "Xaa is Lys or Gln"

(ix) FEATURE:
     (A) NAME/KEY: Modified-site
     (B) LOCATION: 21
     (D) OTHER INFORMATION: /note= "Xaa is Ser, Gly or Arg"

(ix) FEATURE:
     (A) NAME/KEY: Modified-site
     (B) LOCATION: 22
     (D) OTHER INFORMATION: /note= "Xaa is Ile, Met or Leu"

(ix) FEATURE:
     (A) NAME/KEY: Modified-site
     (B) LOCATION: 23
     (D) OTHER INFORMATION: /note= "Xaa is His, Asn, Arg, Ser,
         Pro or Thr"

(ix) FEATURE:
     (A) NAME/KEY: Modified-site
     (B) LOCATION: 24
     (D) OTHER INFORMATION: /note= "Xaa is Ile, Met or Leu"

(ix) FEATURE:
     (A) NAME/KEY: Modified-site
     (B) LOCATION: 28
     (D) OTHER INFORMATION: /note= "Xaa is Arg, Lys or Gln"

(ix) FEATURE:
     (A) NAME/KEY: Modified-site
     (B) LOCATION: 29
     (D) OTHER INFORMATION: /note= "Xaa is Ala or Val"

(ix) FEATURE:
     (A) NAME/KEY: Modified-site
     (B) LOCATION: 30
     (D) OTHER INFORMATION: /note= "Xaa is Pre, Leu, Ile, Met
         or Val"

(ix) FEATURE:
     (A) NAME/KEY: Modified-site
     (B) LOCATION: 31
     (D) OTHER INFORMATION: /note= "Xaa is Tyr, Phe, His or Leu"

(ix) FEATURE:
```

```
        (A) NAME/KEY: Modified-site
        (B) LOCATION: 34
        (D) OTHER INFORMATION: /note= "Xaa is Gly, Lys, Arg or Glu"

(ix) FEATURE:
        (A) NAME/KEY: Modified-site
        (B) LOCATION: 35
        (D) OTHER INFORMATION: /note= "Xaa is Ile, Lys or Arg"

(ix) FEATURE:
        (A) NAME/KEY: Modified-site
        (B) LOCATION: 36
        (D) OTHER INFORMATION: /note= "Xaa is Ile or Thr"

(ix) FEATURE:
        (A) NAME/KEY: Modified-site
        (B) LOCATION: 38
        (D) OTHER INFORMATION: /note= "Xaa is Asp or Tyr"

(ix) FEATURE:
        (A) NAME/KEY: Modified-site
        (B) LOCATION: 40
        (D) OTHER INFORMATION: /note= "Xaa is Arg or Gly"

(ix) FEATURE:
        (A) NAME/KEY: Modified-site
        (B) LOCATION: 43
        (D) OTHER INFORMATION: /note= "Xaa is His or Tyr"

(xi) SEQUENCE DESCRIPTION: SEQ ID NO:11:

Val Gln Leu Asn Glu Ser Val Glu Ile Asn Cys Xaa Arg Pro Xaa Xaa
1               5                  10                  15

Xaa Xaa Xaa Xaa Xaa Xaa Xaa Xaa Gly Pro Gly Xaa Xaa Xaa Xaa Thr
            20                  25                  30

Thr Xaa Xaa Xaa Gly Xaa Ile Xaa Gln Ala Xaa Cys Asn Ile Ser Arg
        35                  40                  45

Ala Lys Trp Asn Asn Thr
        50

(2) INFORMATION FOR SEQ ID NO:12:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

CGCGAATTCT CCATGGTTCA GCTGAACGAA TCTGTTGAC                     39

(2) INFORMATION FOR SEQ ID NO:13:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

CGGACGGGWG CAGTTGATGT CAACAGATTC GTTCA                         35

(2) INFORMATION FOR SEQ ID NO:14:

(i) SEQUENCE CHARACTERISTICS:
        (A) LENGTH: 55 base pairs
        (B) TYPE: nucleic acid
```

```
        (C) STRANDEDNESS: single
        (D) TOPOLOGY: linear (ii) MOLECULE TYPE: cDNA (xi) SEQUENCE DESCRIPTION: SEQ ID NO:14:

ATCAACTGCW CCCGTCCGWA CAAMAASAYC AKAMAGRGMM TSMVCMTSGG CCCGG            55

(2) INFORMATION FOR SEQ ID NO:15:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

ATGTTGCAGT RAGCCTGACS GATGTMGCCG RTTHTTYYGG TAGTGWRSAH ARCTYKACCC       60

GGGCCSAKG                                                              69

(2) INFORMATION FOR SEQ ID NO:16:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

CAGGCTYACT GCAACATCTC TCGTGCTAAA TGGAACA                                37

(2) INFORMATION FOR SEQ ID NO:17:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

CGCGTCGACA GTGTTGTTCC ATTTAGCACG AGAG                                  34
```